(12) United States Patent
Williams et al.

(10) Patent No.: US 8,734,325 B2
(45) Date of Patent: May 27, 2014

(54) OXYGEN THERAPY WITH ULTRASOUND

(75) Inventors: Terry Nelson Williams, Raleigh, NC (US); Paul Edward Schubert, Raleigh, NC (US); Howard E. Purdum, Raleigh, NC (US)

(73) Assignee: Trinity Wound Institute, LLC, Raleigh, NC (US)

( * ) Notice: Subject to any disclaimer, the term of this patent is extended or adjusted under 35 U.S.C. 154(b) by 1442 days.

(21) Appl. No.: 11/759,284

(22) Filed: Jun. 7, 2007

(65) Prior Publication Data

US 2007/0286809 A1    Dec. 13, 2007

Related U.S. Application Data

(60) Provisional application No. 60/811,520, filed on Jun. 7, 2006, provisional application No. 60/842,614, filed on Sep. 6, 2006, provisional application No. 60/861,471, filed on Nov. 29, 2006.

(51) Int. Cl.
*A61N 1/00* (2006.01)

(52) U.S. Cl.
USPC .............................. 600/101; 600/437; 601/2

(58) Field of Classification Search
None
See application file for complete search history.

(56) References Cited

U.S. PATENT DOCUMENTS

| | | | |
|---|---|---|---|
| 4,366,169 A | 12/1982 | White | |
| 5,409,472 A | 4/1995 | Rawlings et al. | |
| 5,743,863 A * | 4/1998 | Chapelon | 601/2 |
| 5,792,090 A | 8/1998 | Ladin | |
| 6,044,845 A | 4/2000 | Lewis | |
| 6,295,990 B1 | 10/2001 | Lewis et al. | |
| 6,312,647 B1 * | 11/2001 | Spears | 422/48 |
| 6,325,769 B1 * | 12/2001 | Klopotek | 601/2 |
| 6,435,189 B1 | 8/2002 | Lewis et al. | |
| 6,537,246 B1 | 3/2003 | Unger et al. | |
| 6,569,099 B1 | 5/2003 | Babaev | |
| 6,649,145 B2 | 11/2003 | McGrath et al. | |
| 6,663,554 B2 | 12/2003 | Babaev | |
| 6,960,173 B2 * | 11/2005 | Babaev | 601/2 |
| 6,964,647 B1 * | 11/2005 | Babaev | 604/22 |
| 7,004,933 B2 | 2/2006 | McDaniel | |
| 7,105,151 B2 | 9/2006 | Unger et al. | |
| 7,201,765 B2 | 4/2007 | McDaniel | |
| 7,216,651 B2 | 5/2007 | Argenta et al. | |
| 7,601,128 B2 * | 10/2009 | Deem et al. | 601/2 |
| 2002/0111386 A1 * | 8/2002 | Sekins et al. | 514/759 |
| 2003/0120204 A1 * | 6/2003 | Unger et al. | 604/82 |
| 2003/0190367 A1 * | 10/2003 | Balding | 424/549 |
| 2004/0057906 A1 * | 3/2004 | Hsu et al. | 424/45 |
| 2004/0087879 A1 | 5/2004 | Mitragotri et al. | |
| 2004/0166171 A1 * | 8/2004 | McGrath et al. | 424/600 |
| 2005/0043654 A1 | 2/2005 | Matsumura et al. | |
| 2005/0228338 A1 | 10/2005 | Greenberg | |
| 2005/0288631 A1 | 12/2005 | Lewis et al. | |
| 2006/0142783 A1 | 6/2006 | Lewis et al. | |
| 2006/0193878 A1 * | 8/2006 | Creech et al. | 424/400 |
| 2007/0055179 A1 * | 3/2007 | Deem et al. | 601/2 |
| 2007/0055181 A1 * | 3/2007 | Deem et al. | 601/2 |

FOREIGN PATENT DOCUMENTS

| | | |
|---|---|---|
| CN | 1404800 A | 3/2003 |
| JP | 2002542841 A | 12/2002 |
| WO | 03061753 A1 | 7/2003 |
| WO | WO 2005105175 A1 * | 11/2005 |

OTHER PUBLICATIONS

Guzmán HR, Nguyen DX, Khan S, Prausnitz MR. Ultrasound-mediated disruption of cell membranes. I. Quantification of molecular uptake and cell viability. J Acoust Soc Am. Jul. 2001;110(1):588-96.*
Guzmán HR, Nguyen DX, Khan S, Prausnitz MR. Ultrasound-mediated disruption of cell membranes. II. Heterogeneous effects on cells. J Acoust Soc Am. Jul. 2001;110(1):597-606.*
Schafer, M.; Dubin, S.; Geshury, A.; Ko, F. Experimental methods for ultrasonically enhanced wound healing. Ultrasonics Symposium, Cannes, France 1994. Proceedings., Nov. 1-4, 1994, v3:1853-1856.*
CN Search Report issued Feb. 18, 2013 in re CN Application No. 200780026637.6 filed Jan. 13, 2009.

* cited by examiner

*Primary Examiner* — Robert A Wax
*Assistant Examiner* — Olga V Tcherkasskaya
(74) *Attorney, Agent, or Firm* — Coats and Bennett, P.L.L.C.

(57) ABSTRACT

A treatment is described for delivering oxygen to tissue, especially hypoxic tissue. A medium saturated with gas is delivered to the tissue. Dissolved gas is transferred from the medium to the tissue. Ultrasound is transmitted to the tissue to enhance the transfer of gas to the tissue.

18 Claims, 4 Drawing Sheets

OXYGEN THERAPY WITH ULTRASOUND

RELATED APPLICATIONS

This application claims the benefit of U.S. Provisional Patent Application Ser. No. 60/811,520 filed Jun. 7, 2006, U.S. Provisional Patent Application Ser. No. 60/842,614 filed Sep. 6, 2006, and U.S. Provisional Patent Application Ser. No. 60/861,471 filed Nov. 29, 2006, which are incorporated herein by reference.

BACKGROUND

According to general industry estimates about 6 million patients suffer from non-healing wounds per year in the United States. These wounds primarily result from diabetes, immobilization, or circulatory problems. Left untreated, these wounds can lead to infection, amputation, or even death.

The healing of compromised tissues usually progresses through distinct stages leading to the eventual restoration of the natural function. As an example, injury to the skin initiates an immediate vascular response characterized by a transient period of vasoconstriction, followed by a more prolonged period of vasodilation. Blood components infiltrate the wound site, endothelial cells are released, exposing fibrillar collagen, and platelets attach to exposed sites. As platelets become activated, components are released which initiate events of the intrinsic coagulation pathway. At the same time, a complex series of events trigger the inflammatory pathways generating soluble mediators to direct subsequent stages of the healing process. These events may result in a transient to prolonged period of oxygen deprivation known as hypoxia in the tissues.

Normally, the healing process of injured tissues is uneventful and may occur regardless of any intervention. However, where an underlying metabolic condition or perpetual insult such as pressure is a contributing factor, the natural healing process may be retarded or completely arrested, resulting in a chronic wound. Trends in modern medical practices have shown that the wound healing of both acute and chronic wounds may be significantly improved by clinical interventions using methods and materials that optimize conditions in the compromised tissues to support the physiological processes of the progressive stages of tissue repair. In dermal wounds, key factors in providing the optimal conditions are the prevention of dead tissue accumulation and the maintenance of an optimal level of moisture and oxygen in the wound bed. All of these factors may be controlled by the management of wound exudate liquid.

A variety of techniques can be applied to facilitate the natural healing process. For example, wound dressings are commonly applied to wounds to control wound site environmental factors such as water vapor, oxygen permeability, bacterial impermeability, and absorption of exudate. Wound care dressing can be tailored to meet specific requirements including conformability to a body portion, selective adherence to a wound bed, and adhesiveness to the skin surrounding the wound site.

Collagen has been used in many forms as wound dressings such as collagen sponges, as described in Artandi, U.S. Pat. No. 3,157,524 and Berg et al., U.S. Pat. No. 4,320,201. However, most of these dressings are not satisfactory for the various types of compromised tissues. Collagen films and sponges do not readily conform to varied wound shapes. Furthermore, some collagen wound dressings have poor liquid absorption properties and undesirably enhance the pooling of liquids.

Another example of dressings that have been developed is hydrocolloid dressings. UK Patent No. 1,471,013 and Catania et al., U.S. Pat. No. 3,969,498 describe hydrocolloid dressings that are plasma soluble, form an artificial eschar with the moist elements at the wound site, and gradually dissolve to release medicaments. Hydrocolloid dressings in general, and the Catania et al. dressings in particular, are subject to a number of drawbacks. The major disadvantages of these dressings include the potential to disintegrate in the presence of excess liquid at the site, and minimal, virtually negligible, control over water and/or oxygen loss from the wound. This latter disadvantage is particularly important, as excess water loss from a wound will cause an increase in heat loss from the body as a whole, potentially leading to hypermetabolism. In addition, hydrocolloid dressings require frequent dressing changes.

Some types of dressings can cause problems that compromise wound healing. For example, thin film dressings such as those described in U.S. Pat. No. 3,645,835, may maintain excessive moisture over a wound bed, contributing to the overhydration or maceration of surrounding skin. Although sponges and gauze support tissue, they require frequent changing, and cause irritation to the compromised tissues during body movement and dressing removal. Calcium alginates turn into a gelatinous mass during interaction with moisture, are difficult to remove completely, and often dehydrate a wound bed due to the hydrophillic nature of the matrix. In addition, none of these devices or materials contributes to maintaining an appropriate level of oxygen to the compromised tissue site. Nor do any of the currently available devices significantly contribute to or support the autolytic debridement phase of wound healing.

A common problem in the management of both acute and chronic wounds is the maintenance of an optimal level of moisture over the wound bed during heavy exudate drainage. This is usually, but not always, during the early stages of healing. Most moist wound dressing technologies such as thin films, hydrocolloid dressings and hydrogels may be typically overwhelmed by exudate moisture during this heavy drainage phase. Management of moisture during heavy exudate drainage often necessitates the use of gauze or sponge packings that wick away excess moisture from the wound bed, thin film coverings that trap exudate liquid over the wound bed, calcium alginate dressings that chemically bind exudate moisture due to the hydroscopic properties of the seaweed extract and other materials that generally restrict exposure to atmospheric oxygen to the wound site.

The removal of exudate from wounds can be enhanced by negative pressure therapy. Briefly, this system consists of a vacuum arrangement that withdraws undesired material through a porous medium that is placed over the wound. While this approach has been shown to be clinically effective in removing exudate and maintaining a moist, sealed environment it does not address the issue of oxygen delivery or other nutrient requirements present in a sub-dermal wound bed's physiology.

Another common problem in tissue treatment is lack of oxygen or other critical nutrients at the wound site. Specifically, oxygen is the single most powerful aid in wound healing. Unfortunately, damage to tissue and vasculature around the wound site may disrupt circulation and limit oxygen transfer at the location where it is most needed. Hypoxemia, caused by disrupted vasculature, is a key factor that limits wound healing. Measurements have shown that the tissue oxygen tension within the wound and surrounding damaged tissues is substantially lower than the normal blood vascular oxygen tension. Whereas the blood vascular oxygen level of 80 to 100 mm Hg is considered normal, the wound environment may have as little as 3 to 30 mm Hg of oxygen. Research has shown that a level of 30 mm Hg or less is insufficient to support the processes of wound repair. Correcting hypoxemia through the administration of supplemental oxygen (O2) may have significant beneficial impact on wound healing in the perioperative and outpatient settings.

Many approaches have been used in an effort to increase the amount of oxygen delivered to compromised tissues. Initial developments to increase the oxygen tension in the compromised tissue environment involved either topical delivery of oxygen to the tissues or chambers in which the blood vascular oxygen tension is substantially elevated so as to also increase to tissue oxygen levels by diffusion. U.S. Pat. No. 4,328,799 describes a hyperbaric oxygen chamber that was constructed such that it fit tightly to a portion of the anatomy. The chamber was then flooded with oxygen gas to higher than atmospheric pressure to increase dissolution of oxygen for delivery to cellular processes. U.S. Pat. Nos. 4,474,571, 4,624,656, and 4,801,291 further describe various improvements for increasing the atmospheric oxygen concentration over the compromised tissue environment. Although these devices are capable of functionally increasing the oxygen level over a wound site, they suffer from the use of cumbersome apparatus, intermittent delivery of oxygen and poor transfer of oxygen from the oxygen-rich atmosphere to the hypoxic tissues.

Another device, disclosed in U.S. Pat. No. 4,608,041, combined delivery of oxygen to tissues with providing an escape pathway for spent gas and wound-derived volatiles. U.S. Pat. No. 4,969,881 extended this development to use less bulky construction by utilizing an oxygen permeable membrane sandwich in which the interior portion was flooded with oxygen, which diffused through the wound contact membrane, but not the upper membrane, to oxygenate tissues. This was further improved in U.S. Pat. No. 6,000,403. These devices represent improvements that overcame much of the bulky characteristics of previous inventions but represent little or no improvement in the transfer of oxygen to hypoxic tissues nor do they constitute improvements in wound contact matrices customarily needed for wound care.

A different approach, used to increase the efficiency of the transfer of oxygen and to eliminate the bulky apparatus was to use nascent oxygen generation near the device. U.S. Pat. No. 5,407,685 provides a device for generating oxygen when the device was applied to a wound. The device disclosed is a bi-layered device where each layer contains a reactant that mixes and generates oxygen once exudate or other bodily-derived material activates the reaction. U.S. Pat. No. 5,736,582 describes the generation of oxygen from hydrogen peroxide for release at or near the skin surface. U.S. Pat. No. 5,855,570 similarly uses an electrochemical reaction to convert oxygen in air to a peroxide or other reactive form of oxygen for delivery to the wound environment. U.S. Pat. No. 5,792,090 uses a reservoir that contained hydrogen peroxide and a catalyst in a device in contact with the wound, such as a hydrogel or polymeric foam. Another approach was disclosed in U.S. Pat. No. 5,086,620 in which pure gaseous oxygen was dispersed by sonic energy into a liquid matrix that was then solidified by cooling to encapsulate the oxygen in minute bubbles.

These devices represent improvements in the delivery of topical oxygen to the wound environment over the hyperbaric chamber. However, each carries significant limitations that have restricted the broad adaptation of the technology of topical oxygenation for care of compromised tissues. Previously described devices do not have a known concentration of oxygen and cannot function independently of atmospheric pressures or temperature to achieve effective oxygen distribution. In addition, the dependence upon activation by body-derived agents is unpredictable so as to make such devices impractical. Other devices are expensive to produce and require specialized equipment. Such devices cannot be used in the production of cold set polymers that are often used for the construction of medical devices used for compromised tissue care Another aspect of tissue treatment is the delivery of active agents to the site of the injury. Active agents for use in compromised tissue treatment may be administered to an individual in a variety of ways. For example, active agents may be administered via methods known to those skilled in the art, such as topically, sublingually, orally, or by injection (subcutaneous, intramuscular or intravenous). Nevertheless, there are drawbacks to many of these methods, and an inexpensive, reliable, localized and relatively pain-free method of administering active agents has not been provided in the prior art.

One common method employed for the treatment of compromised tissues is the topical application of a salve or ointment. Topical application to a wound can be painful. Additionally, in the case of a deeply cavitated wound, an excess of active agent may be required because the agent must diffuse through layers of necrotic tissue and newly forming epidermal tissues. Furthermore, application of topical agents to sites in the interior of the body is highly impractical in that the topical agents are washed off or migrate to other sites. This difficulty in delivering the agent may require the application of an excessive amount of the agent and preclude an accurate determination of the effective amount of active agent delivered.

The oral and sublingual administrations of active agents used in tissue treatment also have their drawbacks. Ingestion of an active agent may result in the agent having negative system-wide effects and possibly disturbing the normal flora, or normal microbial environment, whose presence benefits an individual. Successful absorption of the agent into the bloodstream also depends on several factors such as the agent's stability in gastrointestinal liquids, the pH of the gastrointestinal tract, solubility of solid agents, intestinal motility, and gastric emptying.

Injection of an active agent, a normally painful method of administration, may have the same negative system-wide effects as that of an oral or sublingual administration. Yet more importantly, a danger inherent in the injection of an active agent is that rapid removal of the agent is impossible once it is administered. There is also a risk of transmission of infections and the possibility of vascular injury due to the use of needles. Topical, oral, sublingual and intravenous methods of administration pose several problems when delivering active agents for the treatment of compromised tissues.

What is needed therefore, are methods and compositions for improving treatments for compromised tissue comprising materials having superior exudate management capabilities, together with the ability to deliver active therapeutic agents and participate in the management of oxygen tension and other nutrient requirements around such sites. Methods and compositions are needed that can provide oxygen delivery to any size area of compromised tissue and preferably, may also provide moisture control and delivery of other active agents.

SUMMARY

The present invention provides a method and apparatus to improve the delivery of oxygen and/or other gaseous species into tissue. In one exemplary embodiment, a liquid saturated with an oxygen-containing gas is delivered to a wound area. Dissolved oxygen is transferred from the liquid to the wound tissue. Ultrasound is transmitted to the wound tissue before, during, or after delivery of the medium to enhance the transfer of oxygen to the wound tissue. In one exemplary embodiment, the ultrasound transmissions include frequency components in two distinct frequency bands: a low frequency band to enhance tissue permeability and a high frequency band to enhance diffusion of the oxygen across cell membranes into the cells. The ultrasound transmissions can additionally be pulsed to enhance circulation of blood to the wound tissue. The use of ultrasound enhances method is especially useful in the treatment of hypoxic tissue.

DETAILED DESCRIPTION

Figure 1:
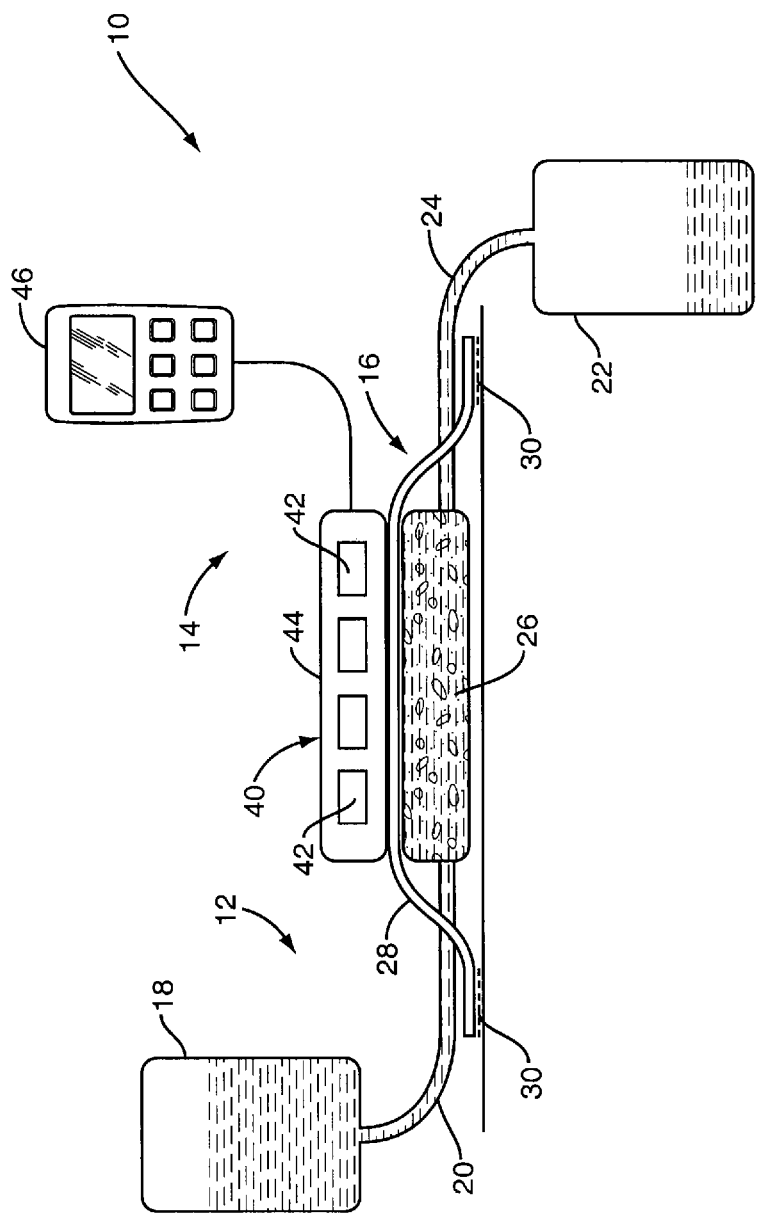
FIG. 1 is a schematic diagram of the tissue treatment system according to one exemplary embodiment.

Referring now to the drawings, FIG. 1 illustrates an exemplary tissue treatment system indicated generally by the numeral 10. The tissue treatment system 10 delivers a liquid carrier saturated with a dissolved gas to the wound area to facilitate wound healing. The tissue treatment system 10 additionally uses ultrasound to enhance the transfer of oxygen from the liquid carrier to the wound tissue.

The tissue treatment system 10 comprises a liquid delivery system 12 and an ultrasound system 14. The liquid delivery system 12 delivers a liquid saturated with oxygen-containing gas to the wound site. With the aid of the ultrasound system 14, the oxygen-containing gas is transferred to the wound tissue. The liquid carrier additionally removes exudate from the wound tissue.

The main components of the liquid delivery system 12 comprise a wound dressing 16, supply reservoir 18 connected to the wound dressing 16 via supply line 20, and a waste container 22 connected to the wound dressing 16 via drain line 24. Wound dressing 16 comprises a foam layer 26 and waterproof membrane 28. The foam layer 26 preferably comprises an open cell polymeric foam, such as polyvinyl alcohol (PVA). In use, the foam layer 26 is placed in contact with the wounded tissue and preferably covers substantially all of the wound. The waterproof membrane 28 is larger than and covers the foam layer 26. While impervious to liquid, the waterproof membrane 28 may comprise a vapor-permeable membrane, such as acetate or polypropylene. A pressure-sensitive adhesive material 30 is applied to the outer margins of the waterproof membrane 28 for adhering the dressing 16 to healthy skin tissue surrounding the wound. Wound dressing 16 as described above can be made in a variety of sizes, allowing medical personnel to select an appropriately-sized wound dressing 16 for treatment.

The supply reservoir 18 contains a liquid carrier such as perfluorocarbon or saline solution that has been saturated or supersaturated with an oxygen-containing gas (e.g., pure oxygen, nitric oxide, carbon dioxide, etc.). Supply line 20 connects the liquid supply reservoir 18 with the wound dressing 16. Drain line 24 connects the wound dressing 16 to the waste container 22. The saturated liquid carrier flows from the supply reservoir 18 through the supply line 20 to the wound dressing 16. The flow rate of liquid may be adjusted as desired. For example, the flow rate may be adjusted in the range of 1-100 milliliters per minute. Some of the oxygen-containing gas in the liquid carrier is transferred to the wound tissue as the liquid flows through the wound dressing 16. From the wound dressing 16, the liquid flows through drain line 24 to the waste container 22.

The liquid supply reservoir 18 and waste container 22 may be arranged for gravity feed operation. Alternatively, positive pressure or vacuum can be used to induce liquid flow through the wound dressing 16.

The ultrasound system 14 facilitates the transfer of oxygen from the liquid carrier to the wound tissue. The ultrasound system 14 comprises a transducer unit 40 comprising one or more ultrasound transducers 42 contained within a sealed housing 44, and a control unit 46. Housing 44 is preferably made of a rigid or semi-rigid material that facilitates transmission of ultrasound. The housing is preferably sealed to allow sterilization of the housing between each use. The transducer unit is disposed above the wound dressing 16 and is oriented to direct ultrasound transmission to the wound tissue.

The ultrasound transducers 42 may comprise an array of multi-frequency transducers capable of generating ultrasound transmissions containing multiple frequency components. Alternatively, the transducer unit 40 may comprise an array of single frequency transducers 42 to produce ultrasound at different frequencies. The control unit 46 controls operation of the transducer unit 40. For example, the control unit 46 may control various parameters of the ultrasound, such as frequency, intensity, phase, duration, and timing of the ultrasound transmissions. The control unit 46 includes a user interface to enable medical personnel to control the settings for these parameters.

In a preferred embodiment, the control unit 46 controls the transducer unit 40 to generate ultrasound in one or more distinct frequency bands. More particularly, the control unit 46 controls the transducer unit 40 to generate ultrasound transmissions containing both a low frequency component in the range of 20-500 kHz and a high frequency component in the range of 500 kHz to 3 MHz. The low frequency component increases the permeability of human tissue to oxygen-containing gases by enlarging the paracellular spaces at the cell junctions. The high frequency component increases the diffusion of the oxygen-containing gas through cellular membranes into cells. While ultrasound is being transmitted to the tissue, the ultrasound transmission can be varied in intensity and/or frequency. For example, the low frequency ultrasound can be varied in the low frequency range, while the high frequency ultrasound can be varied in the high frequency range. Variation in the intensity may be used to vary the depth of penetration of the oxygen or other gaseous species into the tissue.

It is not necessary that ultrasound transmissions be applied continuously during the tissue treatment. For example, ultrasound may be applied for five minutes every one to three hours during tissue treatment. If necessary, the ultrasound transmissions could be applied for longer lengths of time (e.g., 10-15 minutes) and/or at greater frequencies (e.g., every 30 minutes).

In some embodiments, the ultrasound transmission may comprise ultrasound pulses. In this case, the control unit 46 may control factors such as pulse width, pulse frequency, duty factor, and pulse shape. Pulsed ultrasound transmission can be used to enhance both blood circulation in the wound tissue and oxygen transfer into the wound tissue. In one exemplary embodiment, the ultrasound pulses are half rectified through either electrical or mechanical means.

The following examples illustrate exemplary embodiments of the invention. In all of the examples, a perfluorocarbon or saline solution containing 5-30 parts per million of pure oxygen is applied to the wound tissue using the liquid delivery system 12 as described. The examples illustrate different parameters of the ultrasound transmission to facilitate oxygen transfer from the liquid carrier to the tissue.

Example 1

The control unit 46 controls the transducer array 42 to generate low frequency ultrasound in the 20-500 kHz range with an intensity of approximately 0.2 watts/cm$^2$. The ultrasound transmission is pulsed and has a duty factor of 50%. The pulsed ultrasound transmission enhances blood circulation in the wound tissue and increases tissue permeability. The intensity of the ultrasound can be adjusted, depending on the depth of penetration desired.

Example 2

The control unit 46 controls the transducer array 42 to generate high frequency ultrasound in the 500 kHz to 3 MHz range with an intensity of approximately 0.2 watts/cm$^2$. The ultrasound transmission comprises pulsed ultrasound with a duty factor of 50%. The high frequency ultrasound increases diffusion of oxygen-containing gas across cell membranes. The frequency and intensity of the ultrasound can be varied to facilitate specific cell diffusion properties.

Example 3

The control unit 46 controls the transducer array 42 to generate an ultrasound transmission having both a low frequency ultrasound component in the range of 20-100 kHz with an intensity of approximately 0.1 watt/cm$^2$. and a high frequency ultrasound component in the range of 500 kHz to 1 MHz with an intensity of approximately 0.1 watt/cm$^2$. Both the low frequency and high frequency components of the ultrasound transmission are pulsed with a duty factor of 50%. The low frequency component increases tissue permeability, while the high frequency component increases diffusion of oxygen-containing gas across cell membranes. The pulsing increases blood circulation in the wound tissue.

The treatment method described herein can be combined with other treatments. For example, therapeutic agents to facilitate wound healing and to prevent infection can be added to the liquid carrier. Some therapeutic agents require certain levels of oxygen concentration in order to be effective. An example is the antibiotic Vancomycin. The therapeutic agents may be added to the liquid carrier to aid the healing process and to prevent infections.

As discussed above, one application of the present invention is the treatment of wounds. Other applications include preservation of tissue when oxygen supply is lost or significantly impaired. For example, the present invention could be applied to deliver oxygen to hypoxic tissue when adequate blood supply to a person's limb is lost. As another example, the present invention could be used to deliver oxygen to organs for transplant after the organs have been removed from the donor. The present invention may also be applied to cosmetic treatments of the face or skin.

Figure 2:
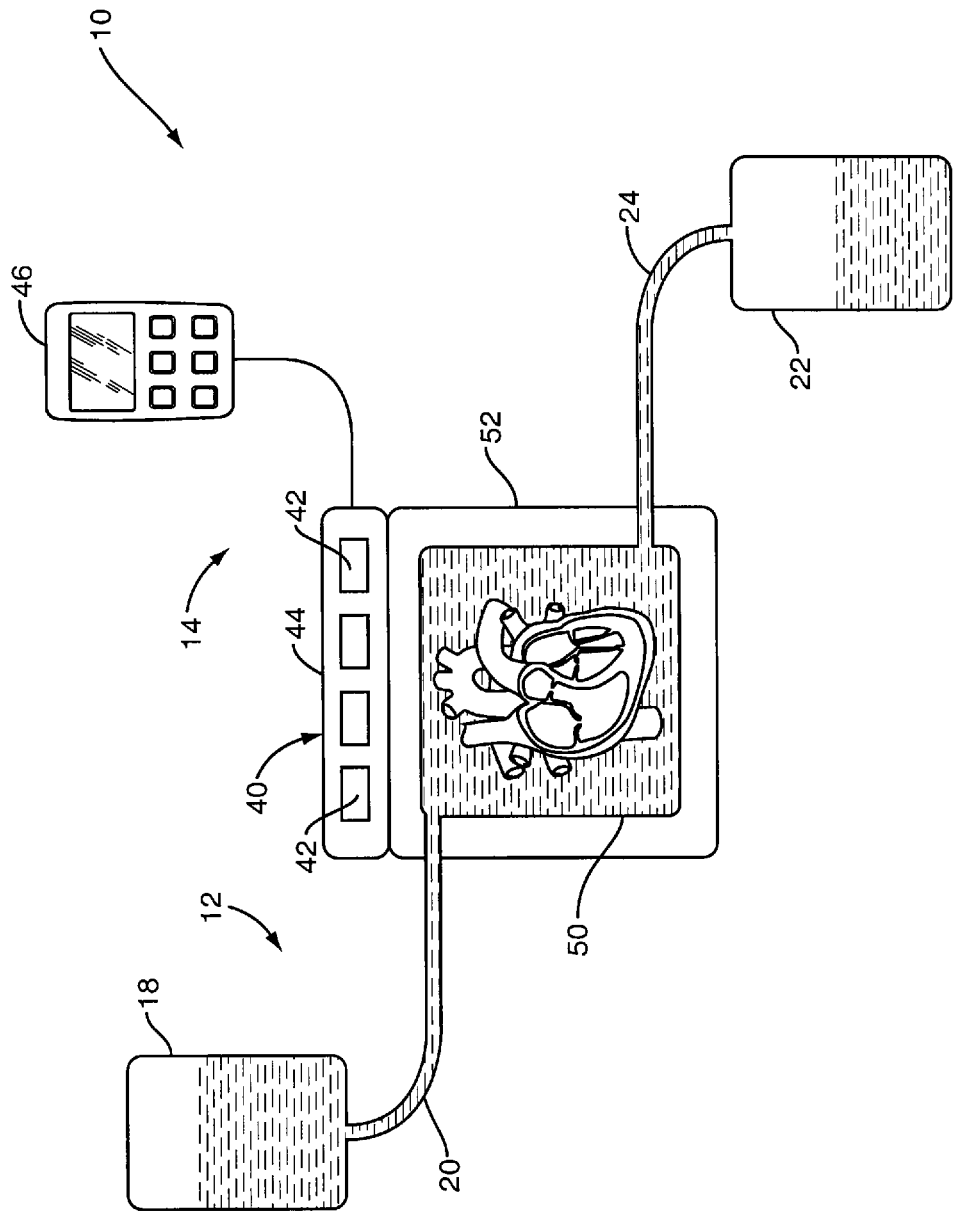
FIG. 2 illustrates an exemplary embodiment for use in preserving transplanted organs.

FIG. 2 illustrates an exemplary embodiment adapted for preservation of organs after the organs are removed from a donor. The organs are placed in a vessel 50 which is supplied with an oxygen containing gas. The organ vessel 50 is housed in a rigid or semi-rigid container 52. Liquid saturated with oxygen or oxygen containing gas is delivered from a supply reservoir 18 to the organ vessel 50. After passing through the organ vessel 50, the liquid carrier drains into a waste container 22. An ultrasound system 14 as previously described is mounted to the container to direct ultrasound to the organ vessel.

Figure 3:
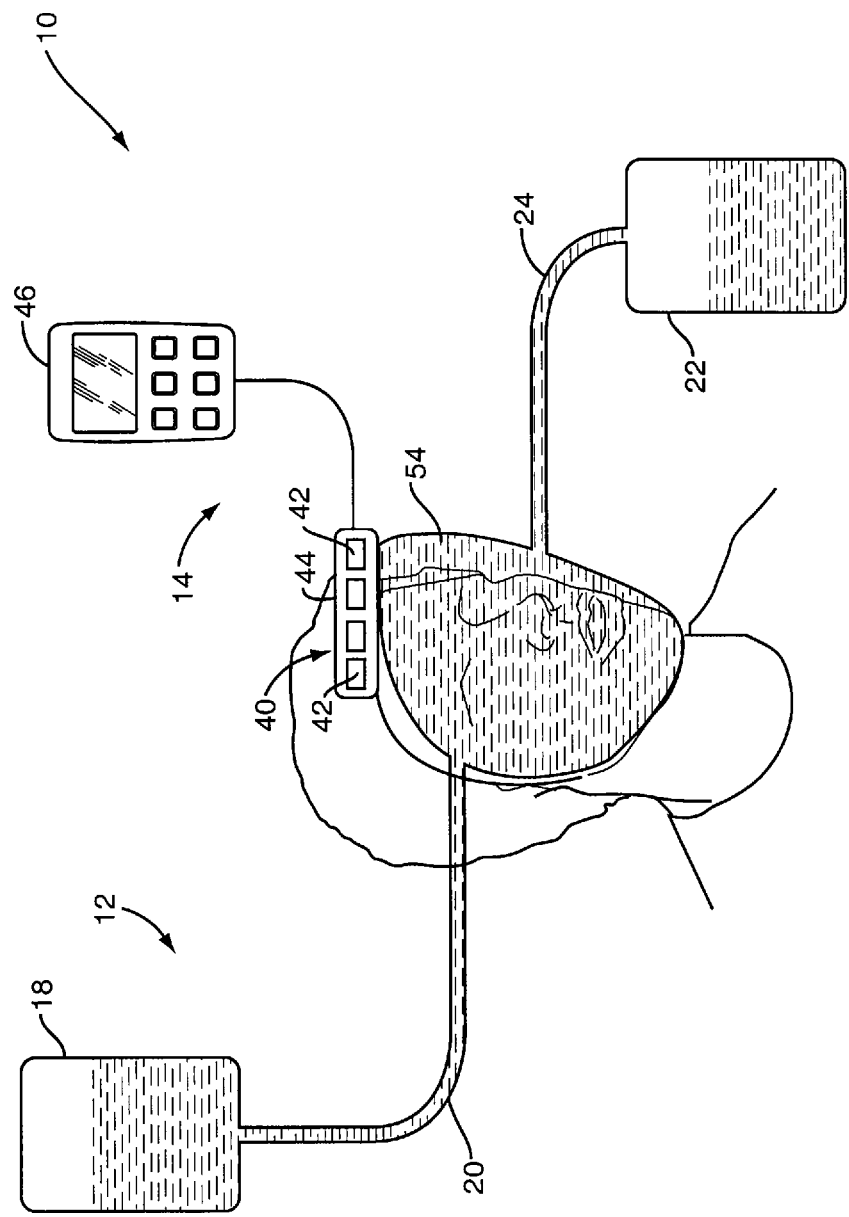
FIG. 3 illustrates an exemplary embodiment for use in cosmetic treatment of the face.

FIG. 3 illustrates an exemplary embodiment adapted for cosmetic treatment of the face. In this embodiment, liquid saturated with oxygen or oxygen containing gas is delivered from a supply reservoir 18 to the face mask 54. After passing through the face mask 54, the liquid carrier drains into a waste container 22. An ultrasound system 14 as previously described is mounted to the face mask 54 to direct ultrasound to the face.

Figure 4:
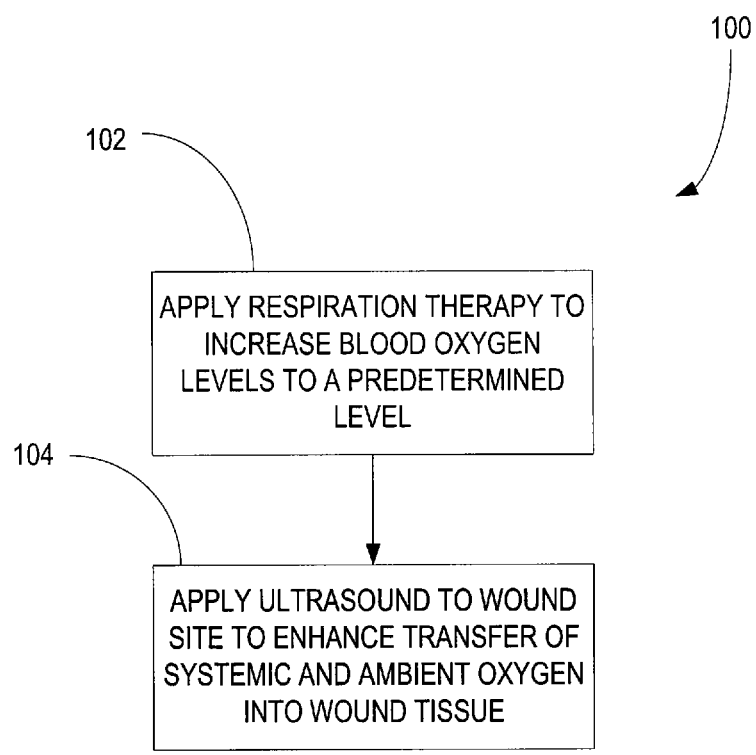
FIG. 4 is a flow diagram illustrating an exemplary method for treating a patient.

FIG. 4 illustrates an exemplary method indicated generally at 100 to enhance the permeability of tissue or cells to ambient or systemic dissolved oxygen in the human body. This method may be used, for example, in the treatment of wounds resulting from diabetes or other illnesses. The first step is increasing the blood oxygen levels in the patient by respiration therapy with a gas containing high levels of oxygen (step 102). The oxygen-containing gas can be delivered, for example, through an oxygen mask. Alternatively, the patients can be placed in an oxygen rich environment, such as an oxygen tent or hyperbaric chamber. Ultrasound is applied to the wound and surrounding tissue to enhance the permeability of the tissue to oxygen, and/or to increase the diffusion of oxygen into cells (step 104). The Ultrasound can be applied before, during, and/or after the respiration therapy. As previously discussed, the ultrasound may contain both a low frequency ultrasound component to increase tissue permeability and a low frequency oxygen component to promote diffusion of the oxygen into the cells.

The present invention may, of course, be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of treating a skin wound comprising:
delivering a medium saturated or supersaturated with a dissolved gas to the skin wound by continuously flowing the medium through a wound dressing applied to the skin wound, wherein the medium contains approximately 5-30 ppm of oxygen; and
directing ultrasound with a frequency in the range of 20-500 kHz to the skin wound before, during or after delivering the medium, wherein the ultrasound is effective to increase the permeability of a wound tissue to said dissolved gas and thereby increase the transfer of said dissolved gas from said medium into said wound tissue.

2. The method of claim 1 wherein the medium comprises saline medium.

3. The method of claim 1 wherein said ultrasound further comprises a high frequency component having a frequency greater than 500 kHz and being effective to enhance diffusion or absorption of oxygen into said wound tissue.

4. The method of claim 1 wherein said ultrasound comprises pulsed ultrasound effective to enhance the wound tissue permeability, the dissolved gas diffusion, or blood circulation to said wound tissue.

5. The method of claim 1 wherein said ultrasound is rectified by electrical or mechanical means to enhance the wound tissue permeability, the dissolved gas diffusion, or blood circulation to said wound tissue.

6. The method of claim 1 wherein said medium includes therapeutic agents that require the presence of the dissolved oxygen or other gaseous species to be effective.

7. The method of claim 6 wherein said therapeutic agents include antibiotics, growth factors, and other compounds beneficial to the healing process in the presence of dissolved oxygen or other gaseous species.

8. The method of claim 1 applied to the treatment of hypoxic wound tissue.

9. A skin wound treatment system comprising:
a delivery system for delivering a medium saturated or supersaturated with a dissolved gas to the skin wound by continuously flowing the medium through a wound dressing applied to the wound, wherein the medium contains approximately 5-30 ppm of oxygen; and
an ultrasound system for generating and directing ultrasound having a frequency in the range of 20-500 kHz to the skin wound and effective to increase the permeability of a wound tissue to said dissolved gas and thereby increase the transfer of said dissolved gas from said medium to said wound tissue.

10. The skin wound treatment system of claim 9 wherein the medium comprises saline medium.

11. The skin wound treatment system of claim 9 wherein said ultrasound further comprises a high frequency component having a frequency greater than 500 kHz and effective to enhance diffusion or absorption of the gas into said wound tissue.

12. The skin wound treatment system of claim 9 wherein said ultrasound comprises pulsed ultrasound effective to enhance the wound tissue permeability, the dissolved gas diffusion, or blood circulation to said wound tissue.

13. The skin wound treatment system of claim 9 wherein said ultrasound is rectified by electrical or mechanical means to enhance the wound tissue permeability, the dissolved gas diffusion, or blood circulation to said wound tissue.

14. The skin wound treatment system of claim 9 wherein said medium includes therapeutic agents that require the presence of the dissolved oxygen or other gaseous species to be effective.

15. The skin wound treatment system of claim 14 wherein said therapeutic agents include antibiotics, growth factors, and other compounds beneficial to the healing process in the presence of dissolved oxygen or other gaseous species.

16. The skin wound treatment system of claim 9 configured for the treatment of hypoxic wound tissue.

17. A method of treating wound tissue comprising:
applying a dressing over the wound tissue to form a closed space covering the wound tissue;
delivering a medium saturated or supersaturated with a dissolved gas to the wound tissue by continuously flowing the medium through the closed space covering the wound tissue, wherein the medium contains approximately 5-30 ppm of oxygen; and
applying ultrasound having a frequency in the range of 20-500 kHz to the wound tissue while flowing the medium through the closed space so as to increase the permeability of the wound tissue to the dissolved gas and thereby increase the transfer of the dissolved gas from the medium into the wound tissue.

18. A wound treatment system for treating wound tissue comprising:
a delivery system for delivering a medium saturated or supersaturated with a dissolved gas to the wound tissue, wherein the medium contains approximately 5-30 ppm of the oxygen, wherein the delivery system comprises:
a wound dressing to cover the wound tissue and form a closed space surrounding the wound tissue, the wound dressing including an inlet opening and an outlet opening;
a supply reservoir containing the medium and connected to the inlet opening of the wound dressing to supply a continuous flow of the saturated medium to the wound dressing; and
a waster container connected to the outlet opening of the wound dressing to receive the medium exiting from the wound dressing; and
an ultrasound system for generating and directing ultrasound having a frequency in the range of 20-500 kHz at the wound tissue effective to increase the permeability of the wound tissue to the dissolved gas and thereby increase the transfer of the dissolved gas from the medium to the wound tissue.

* * * * *